US 6,174,314 B1
United States Patent
Waddell

(10) Patent No.: US 6,174,314 B1
(45) Date of Patent: Jan. 16, 2001

(54) IN SITU PATTELLAR RESECTION GUIDE

(76) Inventor: David D. Waddell, 2900 Hearne Ave., Shreveport, LA (US) 71103

(*) Notice: Under 35 U.S.C. 154(b), the term of this patent shall be extended for 0 days.

(21) Appl. No.: 09/210,848

(22) Filed: Dec. 15, 1998

Related U.S. Application Data

(60) Provisional application No. 60/069,842, filed on Dec. 17, 1997.

(51) Int. Cl.[7] .................................................. A61B 17/58
(52) U.S. Cl. .............................................. 606/88; 606/82
(58) Field of Search ........................... 606/88, 82, 85–87, 606/89–90, 102

(56) References Cited

U.S. PATENT DOCUMENTS

| | | |
|---|---|---|
| 4,633,862 | 1/1987 | Petersen . |
| 5,021,055 | 6/1991 | Burkinshaw et al. . |
| 5,108,401 | 4/1992 | Imsall et al. . |
| 5,129,908 | 7/1992 | Patersen . |
| 5,147,365 | 9/1992 | Whitlock et al. . |
| 5,380,332 | 1/1995 | Ferrante . |
| 5,454,816 * | 10/1995 | Ashbt ..................................... 606/88 |
| 5,486,178 * | 1/1996 | Hodge ................................... 606/82 |
| 5,520,692 | 5/1996 | Ferrante . |
| 5,542,947 | 8/1996 | Treacy . |
| 5,624,444 * | 4/1997 | Wixon et al. ........................... 606/88 |
| 5,667,512 * | 9/1997 | Johnson ................................. 606/88 |

OTHER PUBLICATIONS

Kelly, Michael A., Patellar Component in Total Knee Arthroplasty, in Current Concepts in Primary and Revision Total Knee Arthroplasty, 1996, pp. 153–158, Lippincott–Raven Publishers, Philadelphia, PA, USA.

Wetzner, Steven M., et al., Bone Scanning in the Assessment of Patellar Viability Following Knee Replacement, in Clinical Orthopedics and Related Research, No. 199, Oct. 1985, pp. 215–219, USA.

Dorr, Lawrence D., and Richard A. Boiardo, Technical Considerations in Total Knee Arthroplasty, in Clinical Orthopedics and Related Research, No. 205, Apr. 1986, pp. 5–11, USA.

Brick, Gregory W., and Richard D. Scott, The Patellofemoral Component of Total Knee Arthroplasty, in Clinical Orthopedics and Related Research, No. 231, Jun. 1988, pp. 163–178, USA.

Aglietti, P., et al., Patellofemoral Functional Results and Complications With the Posterior Stabilized Total Condylar Knee Prosthesis, in The Journal of Arthroplasty, vol. 3, No. 1, Mar. 1988, pp. 17–25, USA.

Brick, Gregory W., and Richard D. Scott, Blood Supply to the Patella: Significance in Total Knee Arthroplasty, in The Journal of Arthroplasty, 1989 Supplement, pp. S75–S79, USA.

(List continued on next page.)

Primary Examiner—Michael Buiz
Assistant Examiner—Lien Ngo
(74) Attorney, Agent, or Firm—Charlotte W. Catlett

(57) ABSTRACT

A patella resection guide and a method of resurfacing a patella in situ are provided to achieve accurate placement and functioning of the patellar prosthesis with respect to the other components of the total knee system in total knee arthroplasty. The resection guide includes an adaptor base, a slotted block and a patellar plate. The resection guide is mounted on a trial component such as a femoral component using the adaptor base. The patella is captured and maintained in its non-everted, anatomic position using a three-point fixation surface of the patellar plate. A height adjustment mechanism is included to change the spacial relationship between the guide and attached trial component. The height adjustment mechanism includes a plurality of grooved posts on the base adaptor and ball plungers on the slotted block which engage the grooves when the height is chosen and set.

17 Claims, 10 Drawing Sheets

OTHER PUBLICATIONS

Ritter, Merrill A., et al., Patellofemoral Complications Following Total Knee Arthroplasty: Effect of a Lateral Release and Sacrifice of the Superior Lateral Geniculate Artery, in The Journal of Arthroplasty, vol. 11, No. 4, 1996, pp. 368–372, USA.

Shaw, James A., A Soft Tissue Closure to Minimize Lateral Patellar Subluxation Following Total Knee Arthroplasty, in American Journal of Knee Surgery, vol. 1, No. 2, Apr._, pp. 112–118, USA.

Surgical Techniques and Instrumentation in Total Knee Arthroplasty, Chapter 26, pp. 767–772.

Superposition of the Patellar Gliding Surface on the Femoral Condyle, p. 15.

* cited by examiner

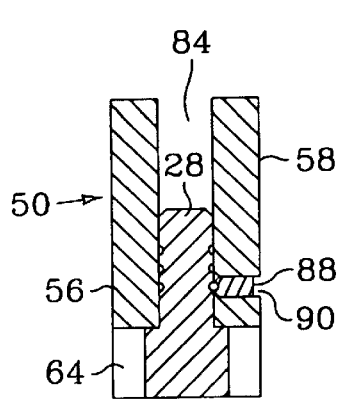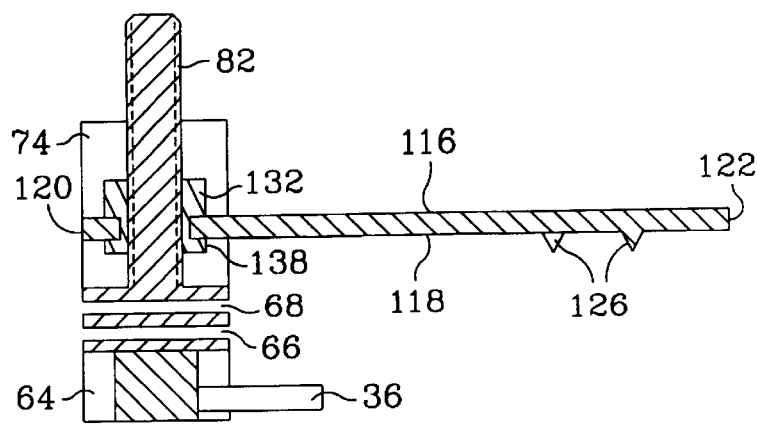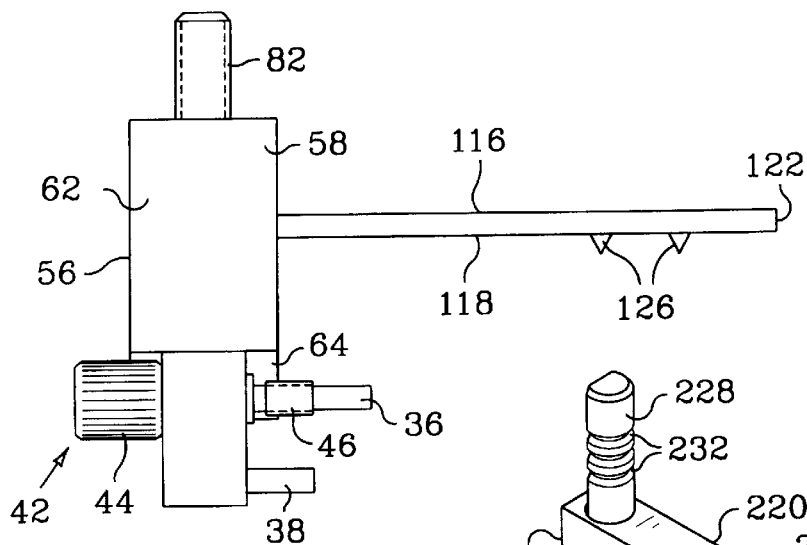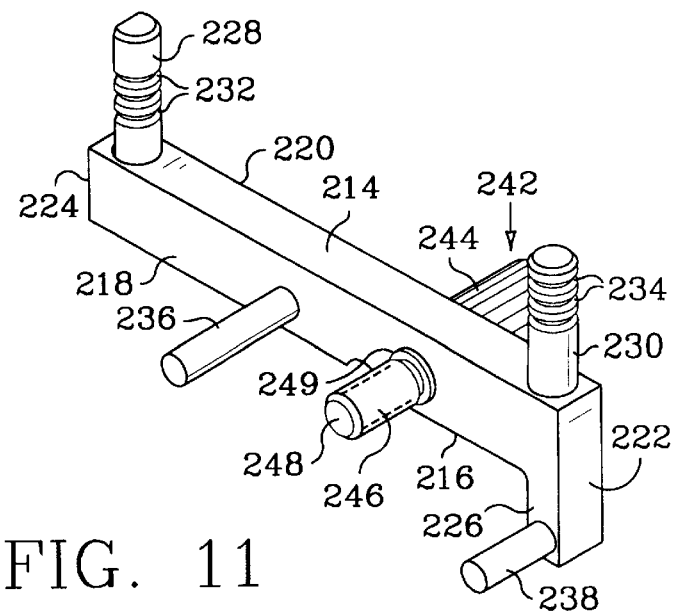
FIG. 8   FIG. 9
FIG. 10
FIG. 11

IN SITU PATTELLAR RESECTION GUIDE

CROSS-REFERENCE TO RELATED APPLICATIONS

This application claims the benefit of U.S. Provisional Application No. 60/069,842, filed Dec. 17, 1997, entitled "Patellar Alignment and Cutting Guide".

STATEMENT REGARDING FEDERALLY SPONSORED RESEARCH OR DEVELOPMENT

Not Applicable

BACKGROUND OF THE INVENTION

1. Field of the Invention

This invention relates to orthopedic surgical tools, and more particularly, to a patellar alignment and cutting guide for use in total knee arthroplasty.

2. Description of Related Art Including Information Disclosed Under 37 CFR 1.97 and 1.98.

The surgical techniques of total knee arthroplasty, including patellofemoral articulation are well known in the art. The leading cause of clinical failure of total knee arthroplasty, or total knee revision, is patella problems such as pain and dysfunction of the patella femoral joint. Many patellar failures are related to patellar misalignment with the femoral and tibial replacement components and with the knee extensor mechanism. When the patella fails, it frequently cannot be so satisfactorily resurfaced, leading to either removal of its components or a patellectomy. These procedures often result in a major compromise to the functioning of the knee.

Another factor in determining ultimate patellar tracking and prosthesis longevity is accurate placement of the patellar prosthesis in the knee. Its articulation with the femoral groove and femoral component is especially integral to the longevity and success of the prosthesis. In order to maintain an acceptable overall patellar thickness and depth in the femoral groove, appropriate bone removal is a necessity, as well as accurate alignment of the cut bone surface and the patellar component in the sagittal, coronal and transverse planes.

One method popularized as a way to increase patellar prosthesis longevity is lateral retinacular release. Lateral retinacular release is used to improve patella tracking when the prosthesis does not track properly after it has been surgically applied. However, several problems associated with lateral release are well known including increased post-operative hemarthrosis and hematoma, Extensive lateral release also increases the probability of a vascular necrosis due to the sacrifice of the patellar branch of the superior lateral geniculate artery.

For a review of the surgical considerations regarding preparation of the to patellar component in total knee arthroplasty, refer to *Patellar Component in Total Knee Arthroplasty*, Kelly, Current Concepts in Primary and Revision Total Knee Arthroplasty, 1996, pages 153–158. Related articles describing the state of the art include the following references: *Bone Scanning in the Assessment of Patellar Viability Following Knee Replacement*, Wetzner, et al, Clinical Orthopedics and Related Research, Number 199, October 1985, pages 215–219; *Technical Considerations in Total Knee Arthroplasty* Dorr and Boiardo, Clinical Orthopedics and Related Research, Number 205, April 1986, pages 5–11; *The Patellofemoral Component of Total Knee Arthroplasty*, Brick and Scott, Clinical Orthopedics and Related Research, Number 231, June 1988, pages 163–178; *Patellofemoral Functional Results and Complications With the Posterior Stabilized Total Condylar Knee Prosthesis*, Aglietti et al, The Journal of Arthroplasty, Vol. 3, No. 1, March 1988, pages 17–25; *Blood Supply to the Patella*, Brick & Scott, The Journal of Arthroplasty, 1989 Supplement, pages S75–S79; *Patellofemoral Complications Following Total Knee Arthroplasty*, Ritter, et al, The Journal of Arthroplasty, Vol 11, No. 4, 1996, pages 368–372; *A Soft Tissue Closure to Minimize Lateral Patellar Subluxation Following Total Knee Arthroplasty*, Shaw, American Journal of Knee Surgery, April 1986, Vol. 1, No. 2; and *Surgical Techniques and Instrumentation in Total Knee Arthroplasty*, James Insall, Surgery of the Knee, $2^{nd}$. Ed., Vol. 2, Chapter 26, pages 767–772.

The success of surgical techniques in total knee arthroplasty and patellar longevity is also influenced by the tools available to the surgeon. Presently, suitable instrumentation systems and cutting guides for the tibial and femoral components are known in the art. For example, see *Surgical Techniques and Instrumentation in Total Knee Arthroplasty*, Chapter 26, pages 767–772. These systems and tools have improved surgeons abilities to implant the components properly and have reduced failures due to improper tibial and femoral condyle component alignment.

There are no known prior art teachings, however, of methods or tools which take into consideration the position of the patella in relation to the femoral condyle at the time of initial patella osteotomy. These cuts are extremely crucial in making sure that the proper relationship of the patella to the femoral groove is maintained and the patellar prosthetic is correctly sited. Instead, known methods and surgical tools for resection of the patella and resurfacing its posterior surface require extension of the knee and eversion of the patella from its anatomically correct position.

References which discuss subject matter related to patella resection include U.S. Pat. Nos. 5,542,947; 5,520,692; 5,380,332; 5,147,365; 5,129,908; 5,108,401; 5,021,055; and 4,633,862, incorporated herein by reference. Use of the alignment guides, clamps, and surgical saws disclosed in these prior art references for removal of the diseased patellar joint surface and for creating the interface for the patellar component are used with the knee extended, the patella everted, and the extensor and connecting tissue pulled away, so the posterior surface of the patella is exposed. Although the aforementioned references disclose how a surgeon typically retracts, reshapes, and profiles the patella, these procedures limit a surgeon's ability to accurately align the patellar component in reference to either the femoral or tibial component. There is no teaching, discussion or disclosure of resurfacing a patella in situ, taking advantage of the anatomic position of the patella with relation to the femoral condyle.

Referring to FIGS. 20 and 21, examples of a femoral component 150 depicting anatomically correct positions of the patella in relation to the femoral articulating surfaces are shown. In FIG. 20, the patella 160 is shown adjacent to the femoral condyle 152 where it articulates with portions of the femoral condyle in the true femorotibial area when the knee is in full flexion. When the knee is in extension, the patella 160 articulates solely with the femoropatellar gliding surface 156 as shown in FIG. 21.

When the patella is everted to make the resurfacing cuts, accurate alignment of the patellar surface with the extensor mechanism and articulating surfaces is inordinately difficult. Therefore, there remains a need for a method of accurate alignment, resurfacing of the patella, and implantation of the patellar component relative to the femoral and tibial components and tools for achieving the same. Such a method and tools would decrease the failures of total knee arthroplasty due to problems with the patellar femoral joint, misalignment with the knee extensor mechanism, and polyethylene wear, thereby improving patellar tracking and increasing prosthesis longevity. The present invention meets these needs.

BRIEF SUMMARY OF THE INVENTION

The present invention consists of a patella resection guide and a method of using the same. It is an object of the present invention to provide a method and apparatus for resectioning the patella while it remains in its anatomically correct position to achieve accurate placement and functioning of the patella prosthesis with respect to the femoral and tibial components and the total knee extensor mechanism.

In the method of the invention, the patellar surface and adjacent component surfaces are determined with the patella in its non-everted anatomical alignment with the femur and tibia. First, the femoral trial, tibial trial, and any other final components are installed and the knee is held in the desired position. In one aspect of the present invention, the knee is held in a flexed position from 0 to 90 degrees with 60 degrees being the preferred position. Next, a resection guide is mounted on either the femoral or tibial component and adjusted for proper alignment in the anterior, posterior and coronal planes, correctly positioning the guide for the individual patella and evaluating the proper depth and angle of resection. In the next step, the posterior of the patella is resurfaced using the appropriate cutting style depending upon the configuration of the total knee system and the individual patella. Next, the patella component is applied.

It is another object of the invention to provide a resection guide which facilitates accurate alignment, cutting and resurfacing of a patella in situ using alternative cutting styles, including straight cuts, angled cuts, or milled curved surfaces.

It is still another object of the invention to provide a resection guide configurable for use with any total knee system. It is yet another object of the invention to provide an alignment and cutting guide configurable for the Hollister-Waddell Total Knee Prosthesis System™.

In a preferred embodiment of the invention, the guide includes an adapter base, a slotted block, and a patellar plate. The adapter base includes a means for attaching the guide to a trial component, such as an installed femoral or tibial trial of a total knee system. In one aspect of the present invention, the adapter base includes an attachment means for mounting the guide on a left knee femoral component. In another aspect of the invention, the adapter base includes an attachment means for mounting the guide on a right knee trial component.

In one embodiment, the attachment means is at least, one support post integral with the attachment surface of the base for insertion into an aperture of the trial component and a first locking means. In one aspect, the first locking means is a locking screw housed within an aperture through the front and attachment surfaces of the base. The first locking screw includes a control knob at the front surface of the base assembly and a shaft at the attachment surface for adjustably securing the guide to the trial component.

In another aspect of the invention, the attachment means includes two support posts integral with the rear surface of the adapter base for insertion into the trial component.

The invention further includes a height adjustment mechanism to position the guide with respect to the knee components. In one embodiment, the height adjustment mechanism includes first and second grooved posts, ball plungers, and a second locking means. The grooved posts extend from the upper surface of the adaptor base and are proximal to its right and left sides. The grooved posts are inserted into post bores which vertically extend through the bottom and top surfaces of the slotted block, proximal to its sides. When the proper height is chosen, the posts are held in position with the ball plungers and the locking means. The ball plungers are housed within apertures which lay horizontally between the right face of the block and the vertical post bore such that a ball of each plunger protudes into the bore for engagement with a groove of the post. When the slotted block is placed on the posts of the base, the plungers click into the grooves.

In one aspect of the invention, the second locking means is a locking screw housed within a horizontal aperture between one side of the slotted block and its proximal vertical bore. When the height adjustment mechanism is secured, the balls of the plungers engage a selected groove of each post and the interior end of the locking screw makes contact with the adjacent grooved post, thereby securing the adapter base to the slotted block.

The slotted block of the resection guide further includes a central window having two interior walls and an interior surface. Each interior wall has a vertical channel between the top of the slotted block and the interior surface. The window also includes a plate retaining post centrally disposed on the interior surface. In one aspect of the invention, the retaining post is a collared screw mounted on the interior surface of the window. In another aspect, the plate retaining post is threaded.

The patellar plate of the resection guide includes means for gripping the patellar surface, opposed stabilizing tabs on its left and right sides, and an aperture through its upper and lower surfaces. The tabs and apertures are proximal to the front end and the means for gripping the patella are on the lower surface, proximal to its rear end. In one aspect, the gripping means are a plurality of prongs. In another aspect, the gripping means includes three conical prongs.

During operation of the invention, the patellar plate is adjustably placed on the slotted block for securing the patella in the desired position relative to the trial component. In one aspect, the plate aperture receives the retaining post of the slotted block and each stabilizing nipple is slidably received within a vertical channel of an interior wall of the window.

In one embodiment, the plate is secured on the retaining post with a third locking mechanism. The third locking mechanism includes a washer on the lower surface of the plate and a rotatable knob with an axial bore. In one embodiment, the bore of the knob is threaded. The knob is mounted within the plate aperture for receiving and securing the plate onto the retaining post.

The slotted block includes at least one horizontal slot between its sides for receiving a resurfacing device. In one aspect of the invention, the block includes two parallel horizontal slots space 3 mm apart. The two horizontal slots allow for ease in resurfacing multiple patellas at standard depths.

Furthermore, according to another embodiment of the invention, the slotted block assembly of the guide includes a means for identifying the proper angle and depth of patella resection. In one aspect, the right and left faces of the slotted block include calibration markings for identifying the proper depth of resection and for identifying the height of the remaining bone after the cut is made.

BRIEF DESCRIPTION OF THE SEVERAL VIEWS OF THE DRAWINGS

The invention will be better understood and its numerous objects and advantages will become more apparent to those skilled in the art by reference to the following drawings, in conjunction with the accompanying, specification, in which:

FIG. 8 is a fragmented cross-sectional view of the present invention taken along lines 8—8 of FIG. 6;

FIG. 9 is a fragmented cross-sectional view of the present invention taken along lines 9—9 of FIG. 6;

FIG. 10 is a right side view of the embodiment of the present invention shown in FIG. 1;

FIG. 11 is a right front perspective view of a right knee adapter base of the present invention;

DETAILED DESCRIPTION OF THE INVENTION

Figure 1:
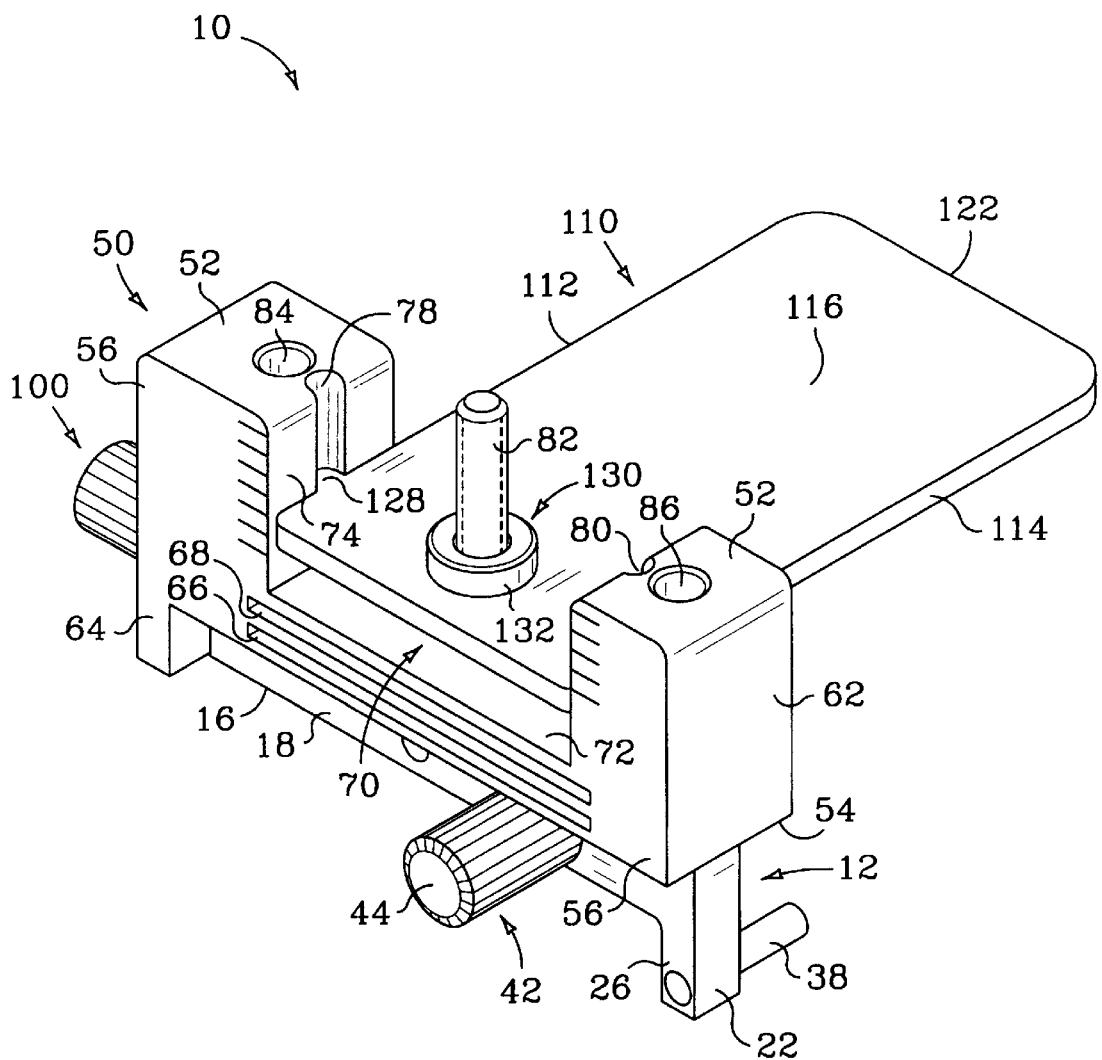
FIG. 1 is a right front perspective view of a resection guide of the present invention fully assembled.
Figure 2:
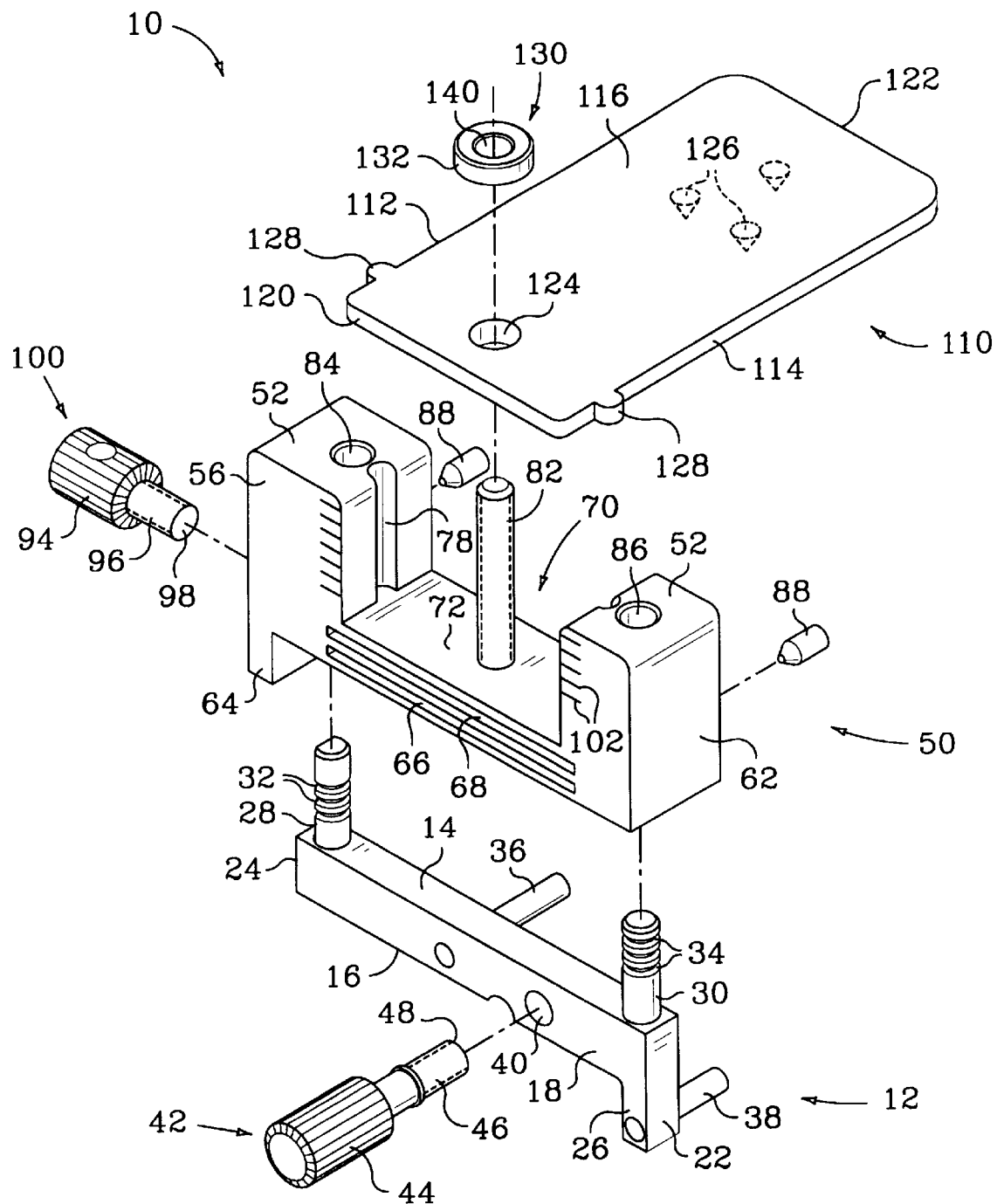
FIG. 2 is an exploded right front perspective view of the embodiment of the invention shown in FIG. 1.
Figure 3:
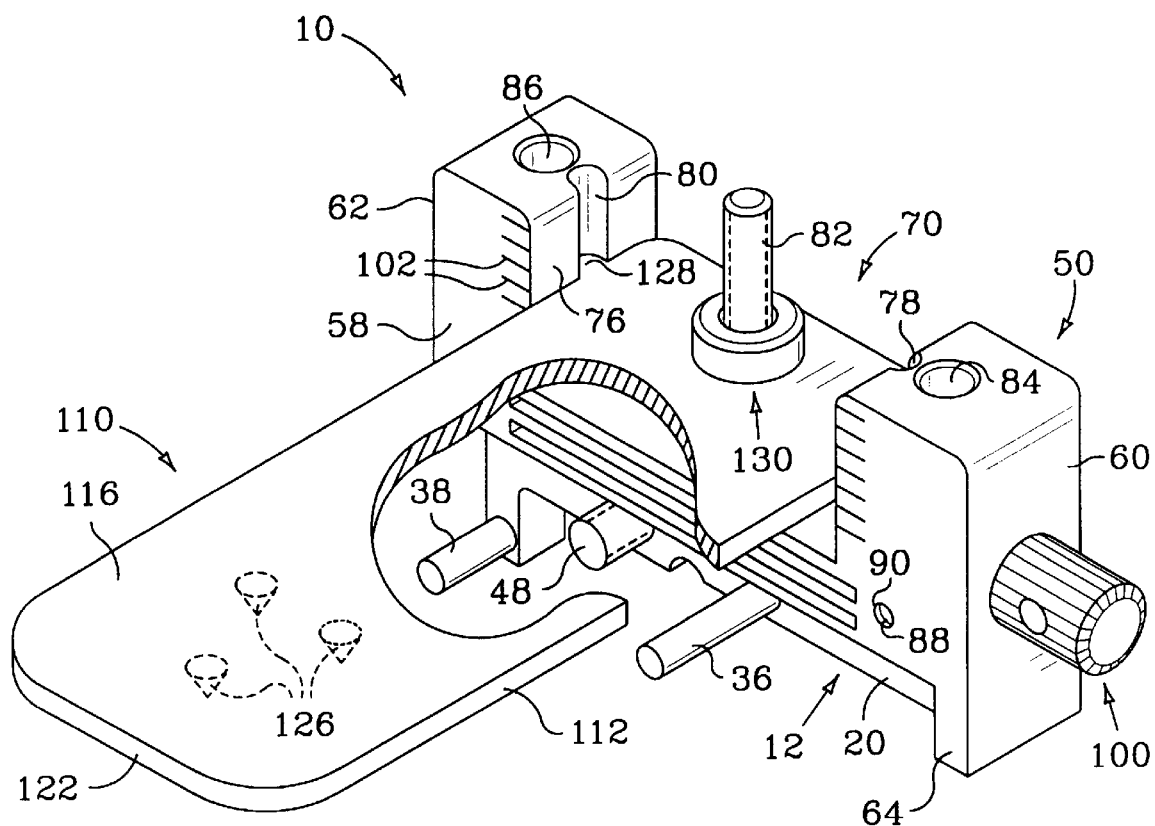
FIG. 3 is a left rear perspective view of the present invention, partially cutaway.

A method and apparatus for resectioning a human patella in a normal anatomic position during a total knee arthroplasty is disclosed. Referring to FIGS. 1–3, a preferred embodiment of a patellar resection guide 11 having an adapter base 12, a slotted block 50 and a patellar plate 110 is shown.

Referring to FIGS. 1–3, and 12–14, the slotted block 50 of the resection guide 10 includes a top 52, bottom 54, left face 56, right face 58, first side 60, second side 62, flange 64, horizontal slots 66, 68, vertical bores 84, 86, apertures 90, calibration markings 102, and a plate retaining window 70. The plate retaining window 70 further comprises a horizontal interior surface 72, interior walls 74, 76, to channels 78, 80, and a plate retaining post 82.

Referring to FIGS. 1–3, and 15–18, the patellar plate 110 of the invention includes sides 112, 114, upper surface 116, lower surface 118, front end 120, rear end 122, aperture 124, gripping means 126, and tabs 128.

The adapter base 12 shown in FIGS. 1–3 is for use with a left knee component and includes an upper surface 14, a lower surface 16, a front surface 18, an attachment surface 20, a right side 22, a left side 24, a flange 26, two grooved posts 28, 30, having grooves 32, 34, and a means for attaching the guide 10 to an installed trial component.

Alternatively, the adapter base 212 of FIG. 11 may be used with a right knee component and includes an upper surface 214, a lower surface 216, an attachment surface 218, a front surface 220, a right side 222, a left side 224, a flange 226, two grooved posts 228, 230, having grooves 232, 234, and a means for attaching the resection guide of the invention to an installed right knee trial component. In this embodiment, the attachment means includes support posts 236, 238 and locking mechanism 242 having a knob 244, shaft 246, end 248 and washer or flange 249.

Using an adapter base such as base 12 or 212, the guide 10 is mounted directly on a component of the total knee system, such as the femoral or tibial trial. This firm fixation onto a trial component ensures proper alignment of the patella with the other components, and allows proper patella angle, patella cut angle, and to depth of cut. Referring to FIGS. 1–3, the attachment means of one embodiment includes support posts 36, 38 on the attachment surface 20 of base adapter 12 and a locking screw 42, housed within aperture 40. Locking screw 42 includes a knob 44 adjacent to the front surface 18 of base 12, shaft 46, and end 48.

Figure 4:
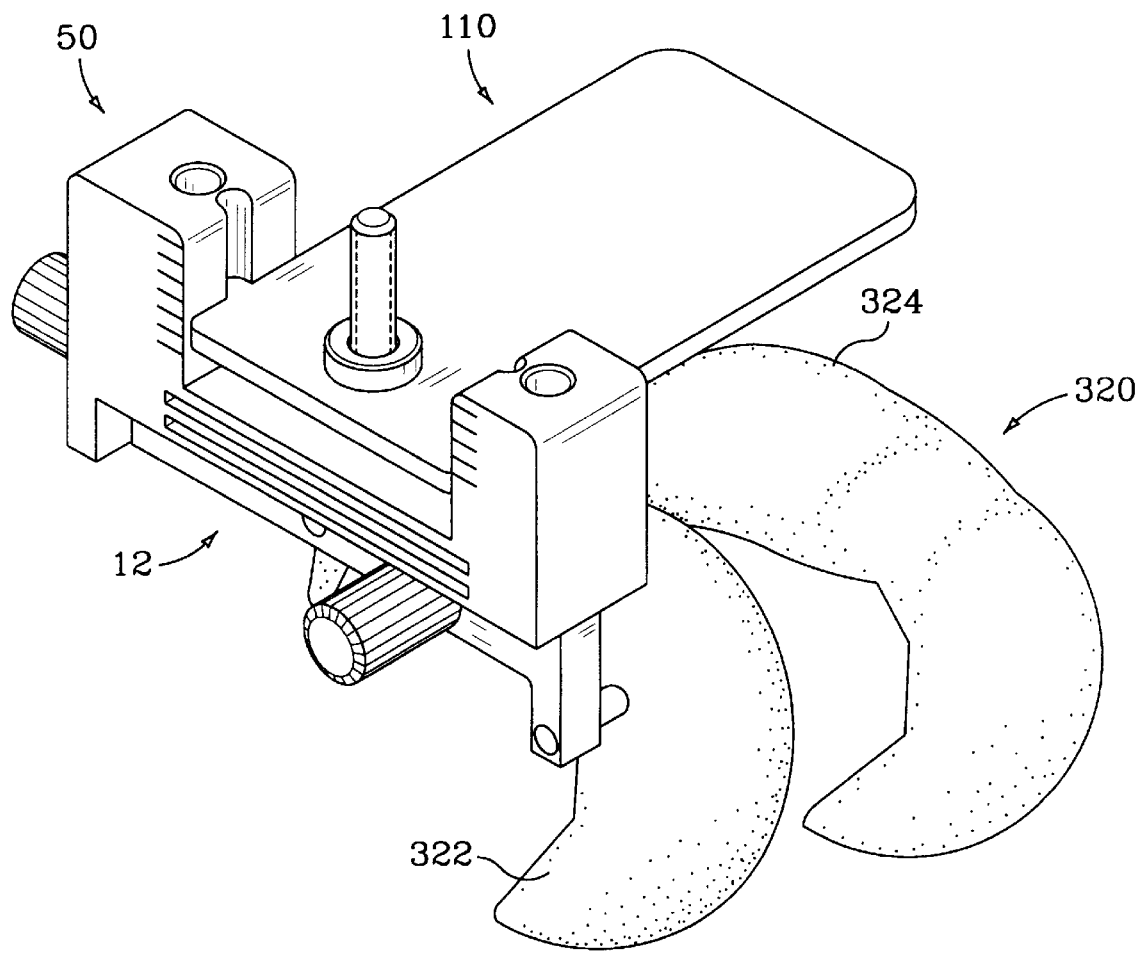
FIG. 4 is a right front perspective view of the present invention fully assembled and attached to the medial side of a femoral component using a left knee adapter base.
Figure 5:
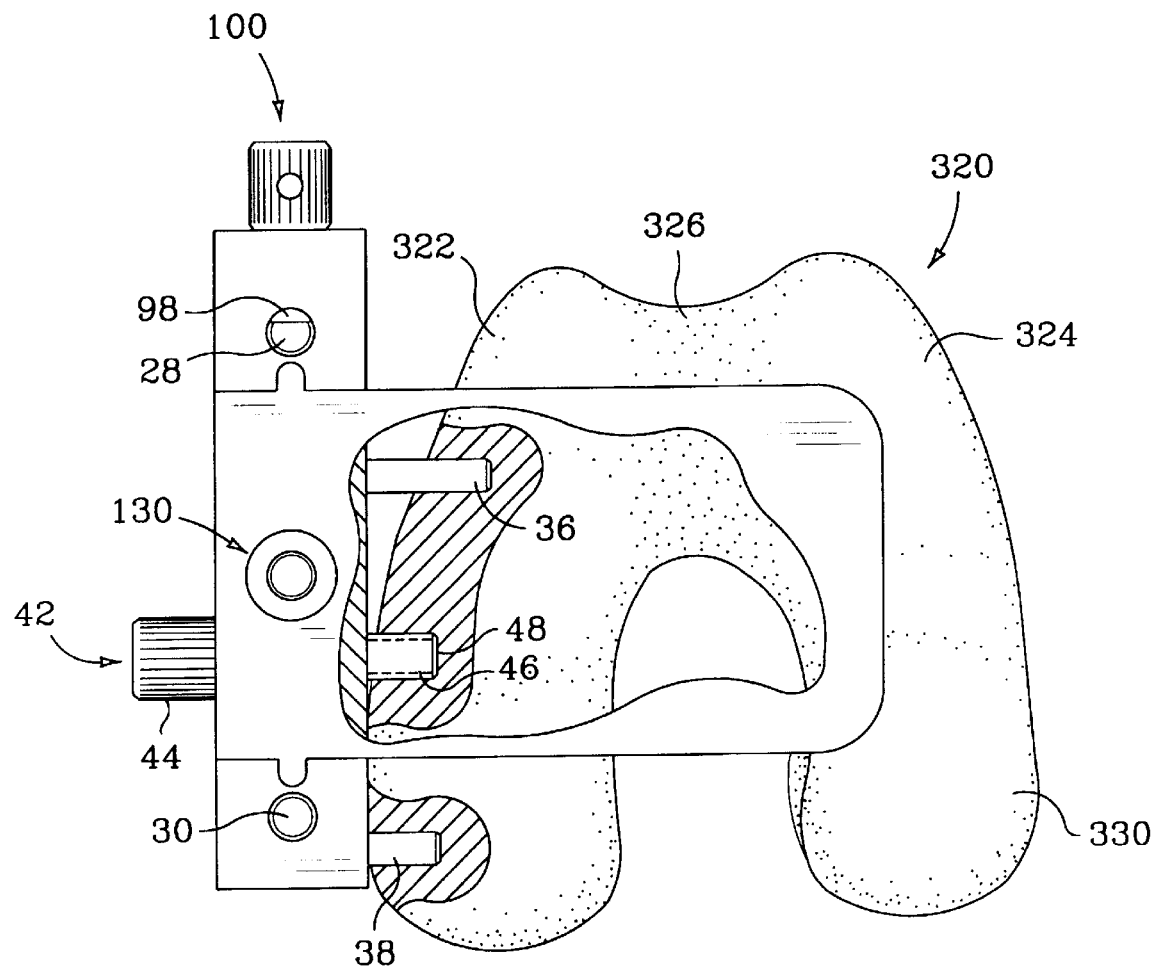
FIG. 5 is a top view of the embodiment of the present invention shown in FIG. 4, partially cutaway.

As shown in FIGS. 4–5, the resection guide is integrally mounted onto a femoral trial 320. The femoral trial 320 includes medial side 322, lateral side 324, articulating surface 326, femoral groove 328, and femoral condyle 330. The guide 10 is shown secured to the angled medial side 322 of a Hollister-Waddell style femoral trial. Specifically, smooth posts 36, 38, and shaft 46, are inserted into apertures within the medial side of the component 320 and secured with first locking means 42.

It will be understood and appreciated by those skilled in the art that the resection guide of the present invention is configurable for mounting on other current total knee systems using alternative attachment and locking means, including non-screwing mechanisms such as clamping or gripping devices.

Resection guide 10 includes a height adjustment mechanism for providing the surgeon with the improved ability to adjust the depth of the patellar cut by changing the position of the slotted block 50 with respect to adapter base 12 and to the attached trial component. As shown in FIGS. 1–3, and 6–8, the height adjustment mechanism includes the two bores 84, 86, disposed through the top and bottom surfaces 52, 54 of the slotted block 50, proximal to the sides 60, 62. When guide 10 is assembled, each bore 84, 86, receives a grooved post 28, 30, respectively, of the adapter base 12. Base 12 is secured to block 50 and the height set at its selected level when ball plungers 88, housed within apertures 90 engage one of a plurality of grooves 32, 34 of posts 28, 30. The second locking mechanism 100, including knob 94, shaft 96, and end 98 is then adjusted to firmly secure base 12 to block 50.

Figure 6:
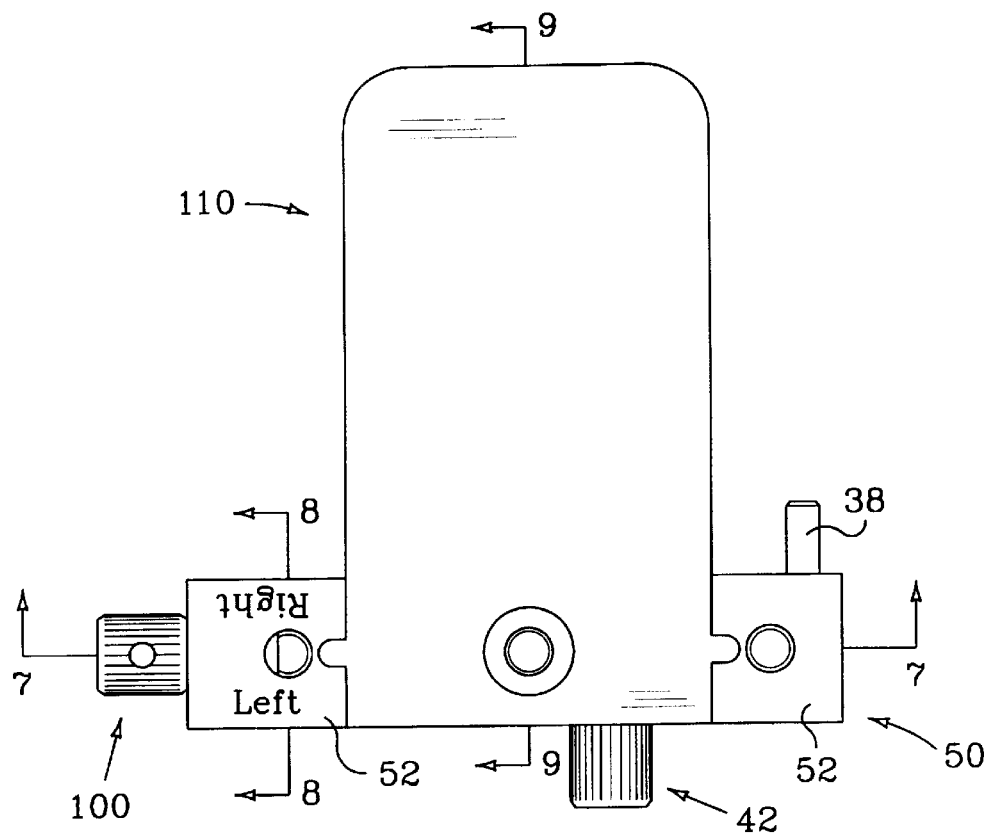
FIG. 6 is a top view of an embodiment of the present invention shown in FIG. 1.
Figure 7:
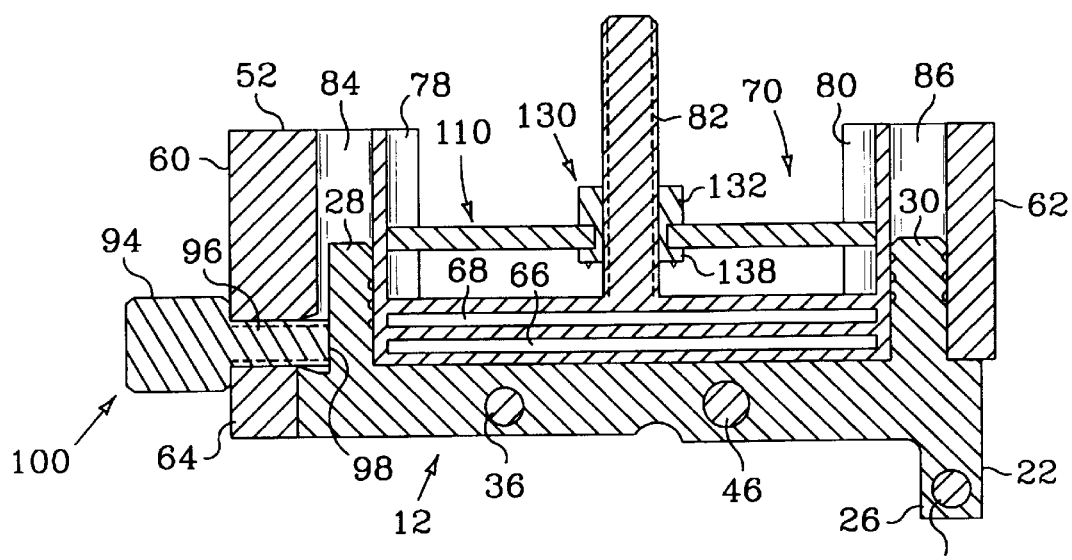
FIG. 7 is a cross-sectional view of the present invention taken along lines 7—7 to of FIG. 6.
Figure 12:
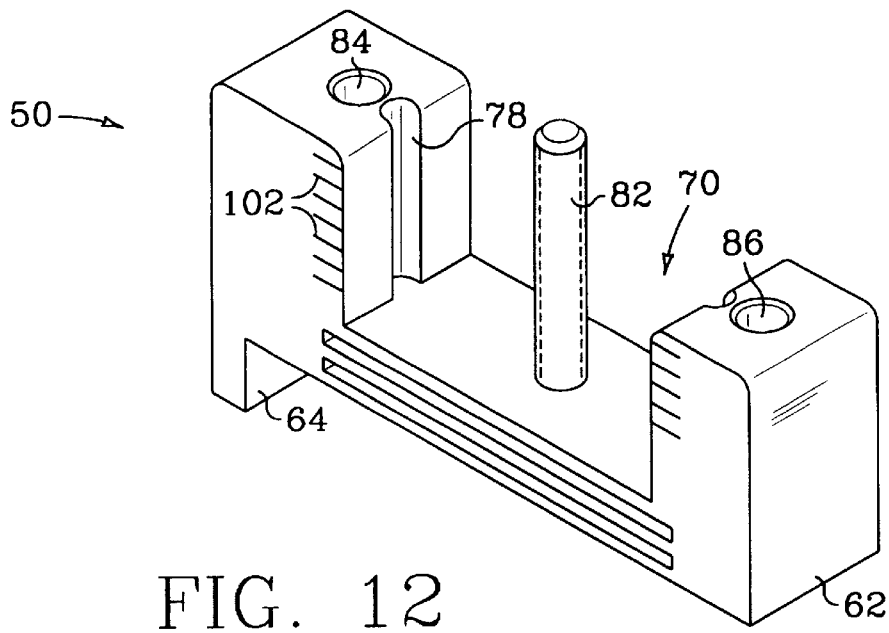
FIG. 12 is a left face perspective view of the slotted block of the present invention.
Figure 13:
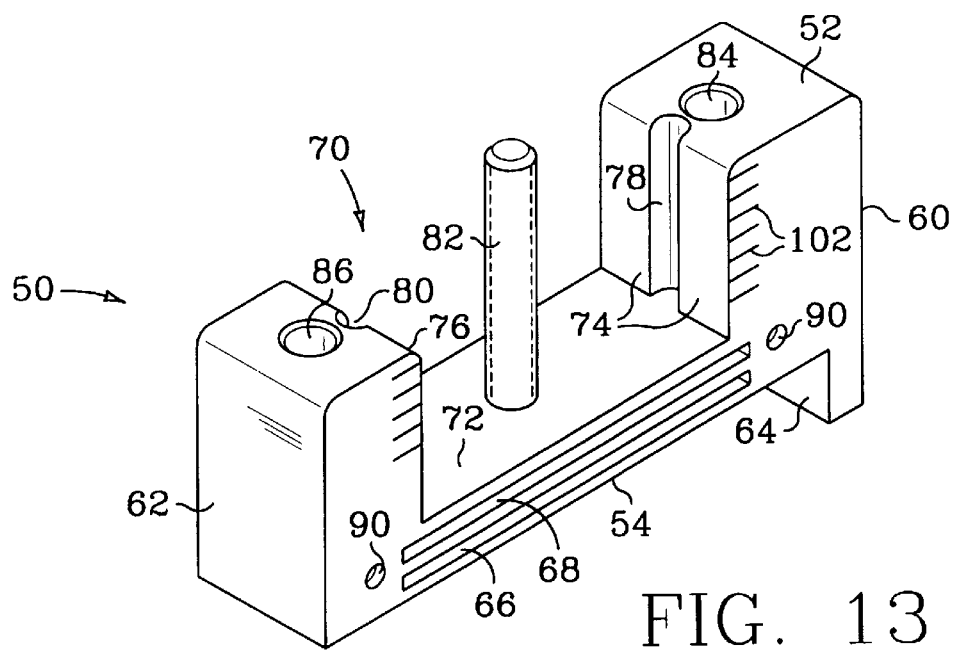
FIG. 13 is a right face perspective view of the slotted block shown in FIG. 12.
Figure 14:
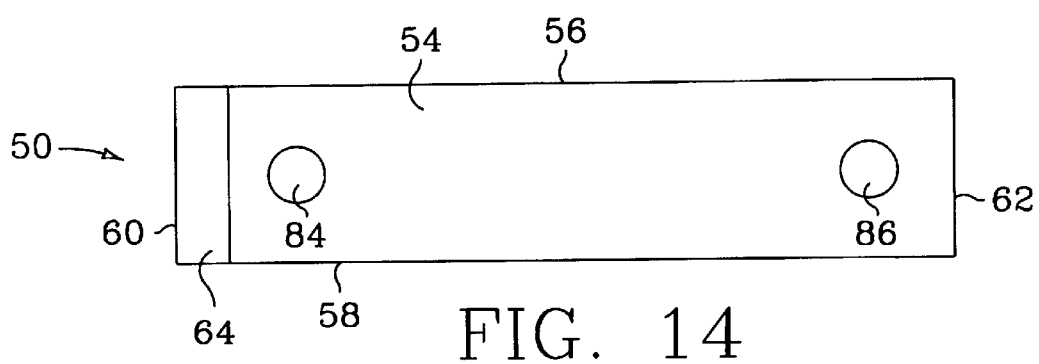
FIG. 14 is a bottom view of the slotted block shown in FIG. 12.
Figures 15, 16:
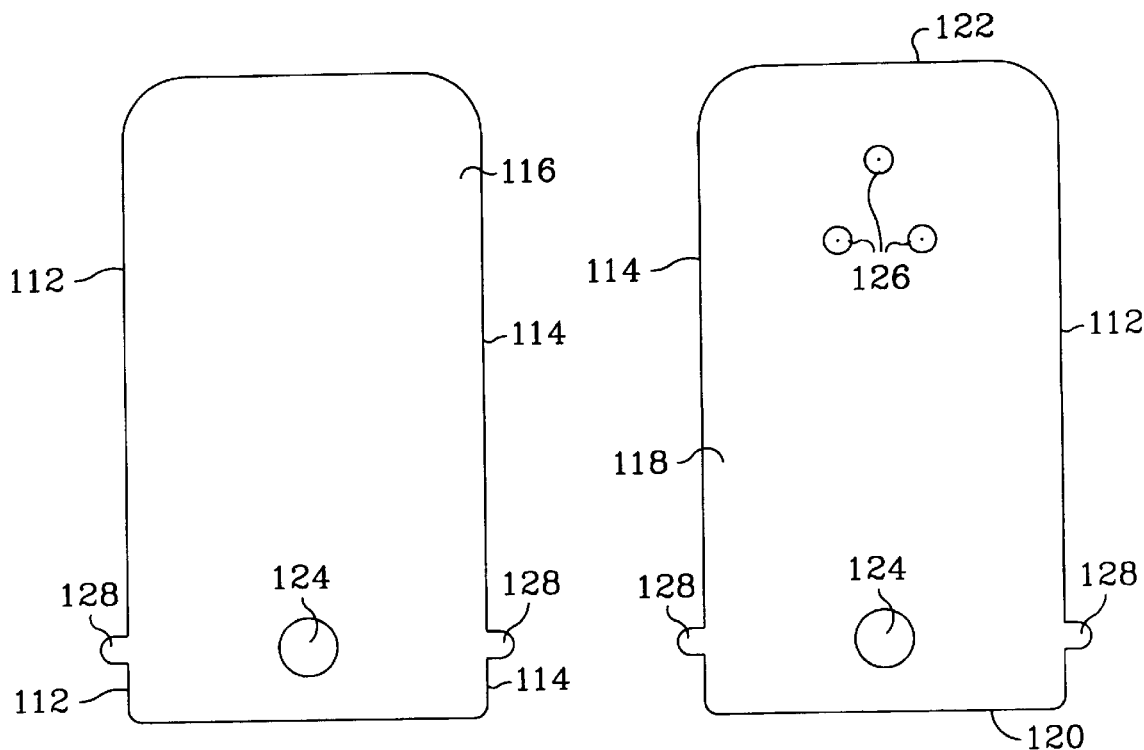
FIG. 15 is a top view of the plate of the present invention.
FIG. 16 is a bottom view of the plate of the present invention.
Figure 17:
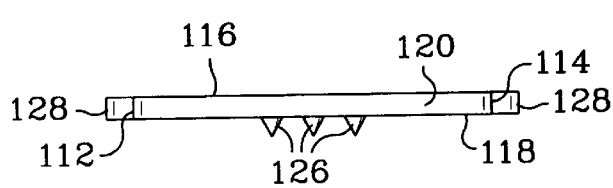
FIG. 17 is a front end view of the plate of the present invention.

Referring briefly to FIGS. 6 and 8, grooved post 28 is shown secured within bore 84 of block 50 having a ball plunger 88 housed within aperture 90 such that the plunger 88 engages a groove 32 of post 28. The use of plungers and grooves provide tactile and audible feedback during height adjustment. It will be understood and appreciated by those skilled in the art that suitable ball-dent mechanisms for use in the present invention include Vlier plungers and similar devices.

The height adjustment mechanism is used by the surgeon in combination with the choice of slots 66, 68 in the slotted block 50 to adjust the depth of resection level. In the preferred embodiment of the invention, two slots 66, 68, are to provided 3 mm apart to accommodate the needs of the individual patella.

Referring back to FIGS. 1–4, the patellar plate 110 is assembled to the slotted block 50 within the central window 70. With the tabs 128 slidably engaged within channels 78, 80, of walls 74, 76, the height of the plate 110 is adjusted on the plate retaining post 82 so that the grippers 126 on the lower surface 118 capture the patella. Once the proper position is chosen, the plate 110 is secured to the post 82 using a third locking means 130.

Figure 19:
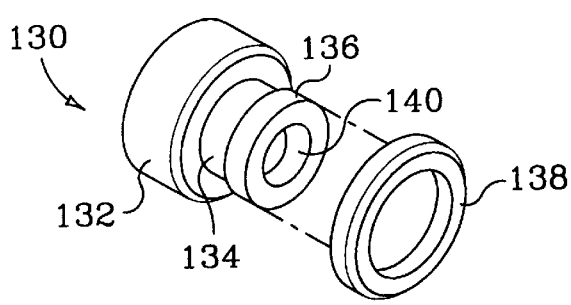
FIG. 19 is a perspective view of a plate knob and washer of the present invention.
Figure 18:
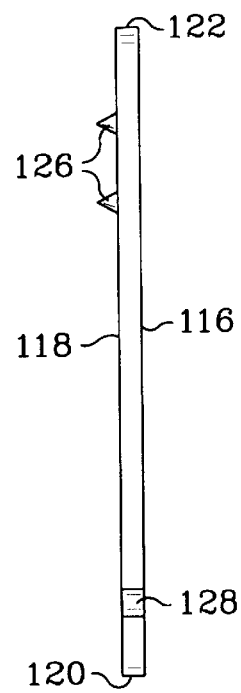
FIG. 18 is a right side view of the plate of the present invention.
Figure 20:
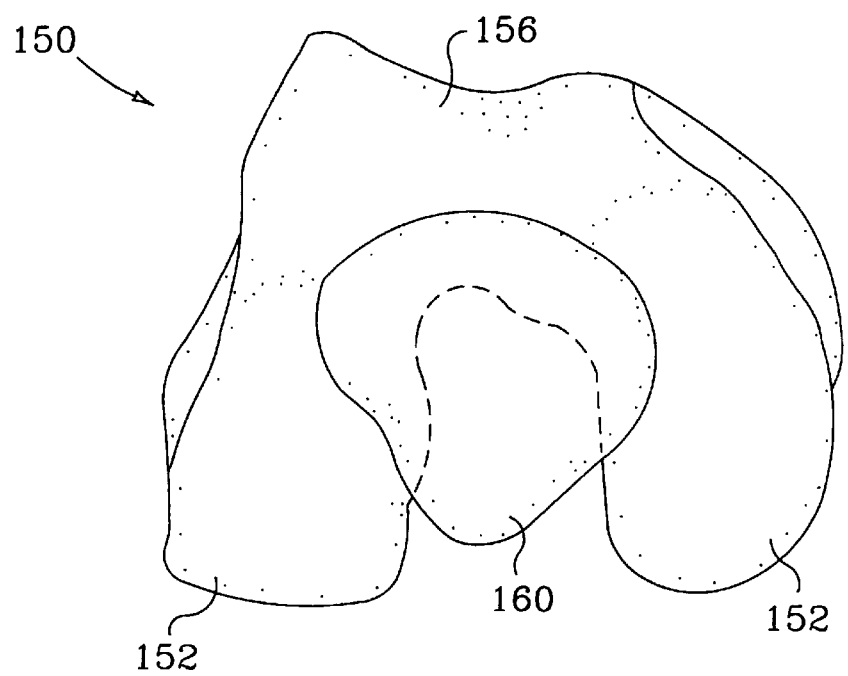
FIG. 20 is a diagramatic view of a femoral trial component including a patella depicting the patella's articulation with portions of the femoral condyle in the femorotibial area.
Figure 21:
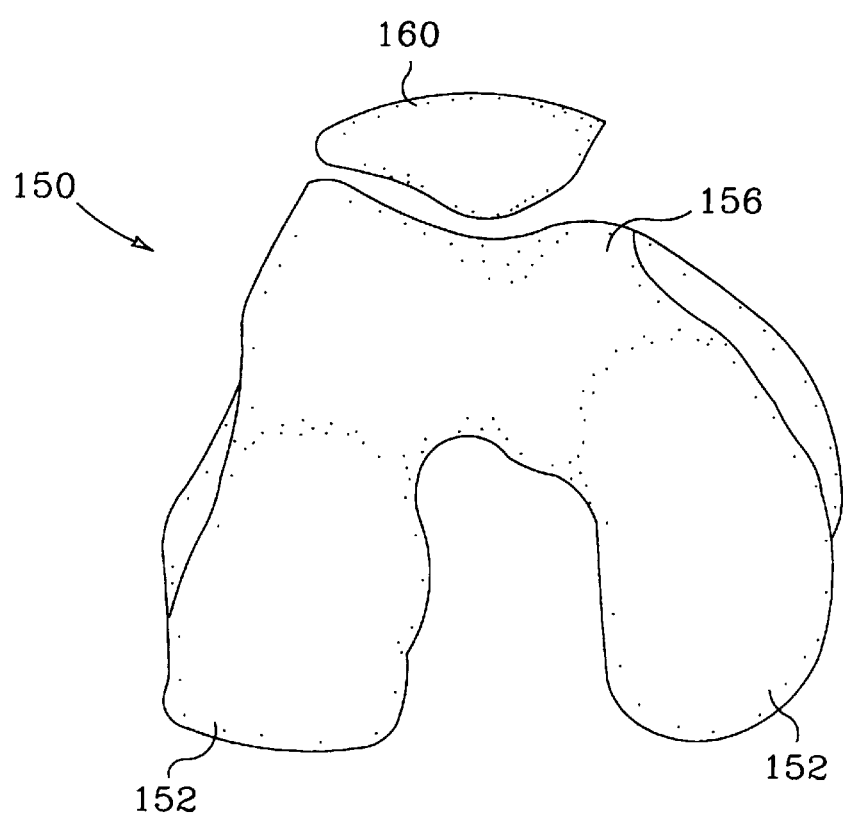
FIG. 21 is a diagramatic view of a femoral trial component including a patella articulating with the femoral patellar surface.

As shown in FIG. 19, locking means 130 includes a washer 138 and a rotatable knob 132 having a shaft 134 and an axial bore 140. In one embodiment of the invention, the retaining post 82 and the axial bore are threaded. As shown in FIGS. 9 and 19, the washer 138 and flange 136 are adjacent to lower surface 118, the shaft 134 is housed within aperture 124, and the knob 132 is adjacent to upper surface 116.

When used with a left adapter base 12, the front end 120 of plate 110 is proximal to left face 56. Alternatively, when used with a right adapter base 212, the front end 120 is proximal to the right face 58.

In the method of the invention, the patellar surface and adjacent component surfaces are determined with the patella in its non-everted anatomical alignment to with the femur and tibia. First, the femoral trial, tibial trial, and any other final components are installed.

Next, the patella is maintained in a non-everted, anatomical position with the knee articulated and the extensor mechanism flexed. When the knee is held in flexion, physiologic tension is placed on the extensor mechanism, improving the alignment of the patella with the extensor mechanism. Typically, the knee should be held in a flexed position from 0 to 90 degrees with 60 degrees being the preferred position. Maintaining the patella in situ, the invention takes advantage of natural factors such as muscular tension, size of the quadriceps mechanism, and tracking angle as determined by factors such as the anterior inferior iliac spine and tibial tubercle.

With all of the anatomic factors in place, the invention is next assembled to a trial component such as the femoral component 320 and the patella is captured with a patellar plate 110. When mounted on the medial side 322 of the femoral trial 320, as shown by example in FIGS. 4 and 5, there is access through the standard medial parapatellar incision. In an alternative embodiment, the guide can be attached to the lateral aspect 324 of the femoral component if a lateral incision is used.

Next, the depth and angle of a resection level are evaluated, taking into consideration the anatomic factors of the individual patella. Optimal resection level varies by implant system. The geometries of the articular surfaces and the patellar fixation region determine the resection depth.

The resection guide is next adjusted to the desired resection depth. This includes using the height adjustment mechanism to change the relationship between the guide and the trial component mounted thereon, and choosing one of the slots in the slotted block for use during execution of the cut.

In the next step, the guide may also be used to determine the medial/lateral tilt and the superior/inferior cut angle on the patella. In this step, the knee is flexed and extended, bringing the patella and prosthesis of the total knee system into optimum position before the cuts are made.

After these adjustments and choices are made, the patella is cut while in its non-everted position. A flat saw cut, angled saw cut or milled surface can be made on the patella, depending on the shape and type of the cutting guide surface and configuration. If a flat cut is to be made, the resulting patellar bone cut can be made perpendicular to the femoral groove with the patella in an anatomic position relative to the femur and the tibia.

Next, the calibrations 102 on the faces of the guide are used to identify the thickness of the remaining bone, providing the surgeon with a reference to judge the thickness of the patella prosthesis to be used.

Advantages of the invention include: having an optimum extensor mechanism system in place thereby maximizing its dynamic function of stabilizing the knee; the guide will not protrude into the resected portion of the distal femur; the guide is positioned adjacent to the femoral trial, close to the patellar bone, resulting in increased cutting accuracy; making a cut which provides an improved patellar prosthesis contour with decreased contact stresses on both the femoral tibial articulation and patellofemoral articulation thereby decreasing polyethylene wear; improving functional performance of the extensor mechanism and maximizing the total knee systems' ability to provide an increased range of motion above current systems.

The method and apparatus of the invention enable the surgeon to make the critical patella cut in the proper reference to the femoral groove, femoral component and other knee components.

It is thus believed that the method, operation and construction of the present invention will be apparent from the foregoing description. While the method and to apparatus shown and described have been characterized as being preferred, it will be readily apparent that various changes and modifications could be made therein without departing from the spirit and scope of the invention as defined in the following claims.

What is claimed is:

1. A patellar resection guide for use during a total knee arthroplasty after installation of the femoral and tibial trial components, comprising:

an adapter base having an upper surface, a front surface, two parallel grooved posts on the upper surface, and an attachment surface having a means for attaching the guide to an installed trial component;

a patellar plate for maintaining the patella in its anatomic position relative to the installed trial component during resurfacing of the patella; said plate having a left side, a right side, an upper surface, a lower surface, a front end, a rear end, and a means for securing the patella in a non-everted position during resurfacing; and a slotted block having a top, a bottom, a left face, a right face, a first side, a second side and at least one horizontal slot between the first and second sides for receiving a resurfacing device.

2. The resection guide of claim 1, wherein the means for attaching the guide to a trial component includes a plurality of support posts on the attachment surface of the adapter base and a first locking mechanism.

3. The resection guide of claim 2, wherein each support post is a smooth peg for insertion into a mounting aperture within the trial component.

4. The resection guide of claim 2, wherein the first locking mechanism is a locking screw having a knob and a threaded shaft for engagement within the trial component.

5. The resection guide of claim 1, further comprising a height adjustment mechanism for changing the position of the guide with respect to the trial component.

6. The resection guide of claim 5, wherein the height adjustment mechanism comprises two bores disposed through the top and bottom surfaces of the slotted block, proximal to the first and second sides, each bore for receiving a grooved post of the adapter base, two ball plungers disposed through the rear face of the slotted block wherein a ball of each plunger protrudes into a bore for engaging a selected groove of each grooved post, and a second locking mechanism.

7. The resection guide of claim 6, wherein the second locking mechanism is a locking screw having a knob and a shaft, said shaft housed within an aperture in a side of the slotted block for preventing slippage of the ball plungers from the selected grooves and securing the adapter base to the slotted block.

8. The resection guide of claim 1, wherein the slotted block includes a central window having two interior walls, an interior surface, and a plate retaining post centrally disposed on the interior surface, each said interior wall having a vertical channel between the top of the slotted block and the interior surface.

9. The resection guide of claim 8, wherein the retaining post is threaded.

10. She resection guide of claim 8, wherein the patellar plate further comprises an aperture through the upper and lower surfaces and opposed stabilizing tabs on the left and right sides, said aperture and tabs proximal to the front end.

11. The resection guide of claim 10, wherein the lower surface of the plate includes a means for gripping the anterior surface of the patella.

12. The resection guide of claim 11, wherein the gripping means includes a plurality of prongs on the lower surface of the patella plate, proximal to the rear end.

13. The resection guide of claim 12, wherein the gripping means includes three conical prongs.

14. The resection guide of claim 10, wherein the patellar plate is adjustably placed on the slotted block for capturing the patella in a desired position relative to the trial component, said plate having the retaining post through the plate aperture and each stabilizing tab slidably received within a vertical channel of the interior walls.

15. The resection guide of claim 14, wherein the patellar plate further comprises a third locking mechanism having a washer and a shaft with an axial bore, said third locking mechanism mounted within the plate aperture for securing the plate into the desired position on the retaining post.

16. A method of resurfacing a human patella during a total knee arthroplasty after installation of the femoral and tibial trial components, comprising the steps of:
   a. maintaining the patella in a normal anatomic position with the knee extensor mechanism flexed;
   b. attaching a patella resection guide to an installed trial component, said guide having a means for securing the patella in a non-everted anatomical position adjacent to the trial component;
   c. capturing the patella in its non-everted anatomically correct position adjacent to a femoral trial component;
   d. evaluating the depth and angle of a patella resection level;
   e. adjusting the patella resection guide to the resection level; and
   f. resurfacing the patella while the patella is secured in its non-everted anatomic position adjacent to the femoral trial component.

17. The method of claim 16, wherein the step of adjusting the guide to the resection level includes the steps of changing the height between the guide and the trial component and choosing a slot in the slotted body to make the cut.

* * * * *

UNITED STATES PATENT AND TRADEMARK OFFICE
CERTIFICATE OF CORRECTION

PATENT NO.   : 6,174,314 B1  Page 1 of 1
DATED        : January 16, 2001
INVENTOR(S)  : David D. Waddell It is certified that error appears in the above-identified patent and that said Letters Patent is hereby corrected as shown below:

Column 1,
Line 12, in the STATEMENT REGARDING FEDERALLY FUNDED RESEARCH OR DEVELOPMENT, please delete "Not Applicable" and replace with:

-- This invention was made with Government support under contract number DE-FG02-96ER62280 awarded by the Department of Energy. The Government has certain rights in this invention. --

Signed and Sealed this

Fifteenth Day of July, 2003

JAMES E. ROGAN
*Director of the United States Patent and Trademark Office*